United States Patent [19]

Ichikawa

[11] 4,393,144
[45] Jul. 12, 1983

[54] METHOD FOR PRODUCING METHANOL

[75] Inventor: Masaru Ichikawa, Yamato, Japan

[73] Assignee: Sagami Chemical Research Center, Tokyo, Japan

[21] Appl. No.: 225,168

[22] Filed: Jan. 15, 1981

Related U.S. Application Data

[63] Continuation of Ser. No. 77,223, Sep. 29, 1979, abandoned.

[30] Foreign Application Priority Data

Sep. 20, 1978 [JP] Japan .................................. 53-114538

[51] Int. Cl.$^3$ ...................... C07C 27/06; C07C 29/15; C07C 31/04
[52] U.S. Cl. .................................. 518/715; 518/717; 518/714
[58] Field of Search ................................ 518/715, 717

[56] References Cited

U.S. PATENT DOCUMENTS

| | | |
|---|---|---|
| 1,681,753 | 8/1928 | Storch . |
| 4,119,656 | 10/1978 | Poutsma et al. . |
| 4,289,709 | 9/1981 | Kaiser .................................. 518/717 |
| 4,289,710 | 9/1981 | Kaiser .................................. 518/717 |

FOREIGN PATENT DOCUMENTS 1366367 9/1974 United Kingdom ................ 518/713

OTHER PUBLICATIONS

Ryndin et al., J. of Catalysis, 70, 287-297, (1981).
Shokubai (catalyst), vol. 21, No. 4, 1979, pp. 253-255.

*Primary Examiner*—Howard T. Mars
*Attorney, Agent, or Firm*—Sughrue, Mion, Zinn, Macpeak & Seas

[57] ABSTRACT

A method for producing methanol which comprises reacting a gas containing a carbon oxide and hydrogen in the presence of a catalyst comprising palladium supported on at least one oxide of metal selected from the group consisting of the metals of the Group IIa and Group IIIa of the short form of the Periodic Table.

3 Claims, No Drawings

METHOD FOR PRODUCING METHANOL

This is a continuation of application Ser. No. 77,223, filed Sept. 29, 1979, now abandoned.

BACKGROUND OF THE INVENTION

1. Field of the Invention

This invention relates to a method for producing methanol from a carbon oxide selected from the group consisting of carbon monoxide and carbon dioxide and hydrogen gas. More particularly, this invention relates to a method for producing methanol which comprises reacting a gas containing (1) a carbon oxide selected from the group consisting of carbon monooxide and carbon dioxide and (2) hydrogen gas in the presence of a catalyst comprising palladium supported on at least one metal oxide selected from the group consisting of the metals of the Group IIa and Group IIIa of the short form of the Periodic Table.

2. Description of the Prior Art

A typical method for producing methanol from a synthetic gas which has conventionally been practiced on an industrial scale comprises reacting the synthetic gas under a pressure of 300 to 350 atms. at a temperature of 300° to 400° C. in the presence of a catalyst comprising zinc oxide and chromium oxide ($ZnO\text{-}Cr_2O_3$), as disclosed in German Pat. Nos. 415,686 and 462,837. Also, a method for producing methanol as described above but using a catalyst where an appropriate amount of copper is added to the above catalyst ($ZnO\text{-}Cr_2O_3\text{-}Cu$) and using a pressure of 50 to 150 atms. and at a temperature of 250° to 300° C. has been known, as disclosed in Japanese Patent Publication No. 8266/55.

These conventional synthetic methods for producing methanol using a catalyst is effectivve to a certain degree but is still required to be improved in the process technique since the reaction of these methods should be operated at a high pressure and at a high temperature. In fact, the improved method for the synthesis of methanol using the Cu-containing catalyst as described above is considered to have been developed as a result of study on reducing pressure and temperature in the operation of methanol synthesis.

However, a multi-component catalyst containing Cu has a disadvantage in that it tends to be poisoned with sulfur or nitroge-containing compounds which are present even in a small amount in the synthetic gas as impurities whereby the life of catalyst is shortened. The synthetic gas which is presently available in industry from the naphtha origin generally has a gas pressure of 15 to 30 atms. and can be further pressurized to about 50 atms. by the rotatory compression method. The methanol synthesis using the synthetic gas of such low to middle pressure range as a raw material is expected to be an efficient industrial technology for the methanol synthesis in future.

Hitherto, palladium powder or palladium metal tips have not been considered to be an effective catalyst for the synthetic gas conversion since they are inactive to the $CO\text{---}H_2$ reaction or they only function as slightly promoting the methane formation in the $CO\text{---}H_2$ reaction, as described in F. Fischer, H. Tropsch, P. Dilthey, Brennstoff-Chem., 6, 265 (1925). For example, in the reaction of a mixed gas of $CO$ and $H_2$ under atmospheric pressure at a temperature in the range of 200° to 300° C. using a palladium catalyst prepared by supporting palladium on an alumina carrier, the production of methane and a small amount of hydrocarbons of $C_2\text{-}C_5$ is promoted, but oxygen-containing compounds useful as industrial raw materials such as methanol and the like are not produced at all, as reported in M. A. Vannice, J. Catal, 37, 449 (1975) or only several percent of the consumed carbon monoxide is converted into methanol under reaction conditions using a mildly low pressure of 5 to 25 $kg/cm^2$ and a high $CO/H_2$ ratio, as reported in Belgian Pat. No. 849–121 (1977).

DETAILED DESCRIPTION OF THE INVENTION

As a result of extensive studies on the reactions of synthetic gas using a catalyst prepared by supporting palladium on a wide variety of metal oxides as carriers, it was found that methanol can be produced selectively and with high conversion ratio under mild reaction conditions at atmospheric pressure to 10 atms. at a temperature of about 50° to about 350° C. only when an oxide of metal selected from the group consisting of the metals of the Group IIa and Group IIIa of the short form of the Periodic Table is used as a carrier for palladium. It was also found that the reaction of synthetic gas under the same reaction conditions as above but using a palladium catalyst supported on an oxide of other metals, for example, $\gamma\text{-}Al_2O_3$, $SiO_2$, $SnO_2$, $TiO_2$, $ZnO_2$, $WO_3$ and the like, produces predominantly methane as main product and results in less than several percent of selectivity to methanol and very low conversion ratio of carbon monoxide, as described hereinafter in detail in Reference Example.

In a preferred embodiment of the present invention, the methanol production velocity in the $CO\text{---}H_2$ reaction under a mildly low pressure (0 to 60 $kg/cm^2$) using a palladium-lanthanum oxide catalyst or palladium-magnesium oxide catalyst according to the present invention which showed an excellent catalytic performance in the study of methanol production was found to be superior in terms of the specific activity per unit volume of the catalyst, as compared with the methanol production velocity obtained by using the $ZnO\text{-}CR_2O_3$ catalyst which is now widely used in the methanol production on an industrial scale. Also, these preferred catalysts used in the method according to the present invention showed an excellent selectivity to methanol higher than 90%.

Since the catalyst used in the method of the present invention exhibits an optimum conversion ratio and a selectivity at a relatively low reaction temperature, i.e., about 50° to about 350° C., and further exhibits a specific catalytic performance for methanol synthesis, it will be apparent to one skilled in the art that the catalyst of the present invention essentially differs from conventional palladium catalyst supported on carrier and is particularly useful for the methanol synthesis.

In preparing the catalyst used in the present invention, a palladium salt such as palladium chloride, palladium nitrate, palladium acetate, palladium oxalate, etc., is dissolved in water or a palladium organometallic compound such as palladium acetylacetonate, etc., is dissolved in an organic solvent such as benzene, tetrahydrofuran, acetone and the like to prepare a solution of a palladium salt having a predetermined concentration, i.e., 1 to 10 w/v%. To the resulting solution is then added at least one oxide of metal selected from the group consisting of metals of the Group IIa and Group IIIa of the short form of the Periodic Table, and the mixture is stirred to immerse in the solution. The solvent is then removed and the residue is dried. The resulting supported palladium salt is then reduced in a hydrogen atmosphere at room temperature (about 25° C.) to 550° C. for a period of about 1 to about 20 hours to obtain the desired catalyst. The reduction of the supported palladium salt can be achieved by any conventional procedure for chemically reducing a metal salt such as (1) reduction with hydrazine, (2) reduction with an aqueous solution of formaldehyde, (3) reduction with a hydride such as sodium borohydride, etc., which are well known in the art.

The ratio of palladium supported by a carrier relative to the amount of the carrier can theoretically vary widely, but in considering the surface area of carriers (about 1 m$^2$/g to 100 m$^2$/g), the amount of palladium supported by the carrier can range 50 to 0.0001% by weight, with preferred range being from 10 to 0.01% by weight from the economical standpoint for maintaining the high selectivity.

Examples of metal oxides selected from the group consisting of the metals of the Group IIa and Group IIIa of the short form of the Periodic Table are berylium oxide, magnesium oxide, calcium oxide, barium oxide and the like and lanthanum oxide, neodymium oxide, yttrium oxide, cerium oxide and the like, respectively. These metal oxides can be used alone or as a combination of two or more metal oxides.

The reaction for the production of methanol according to the present invention can be carried out using a closed circulating reactor, a differential circulating flow reactor or an atmospheric or pressured flow fixed-bed reactor. In carrying out the reaction, the catalyst is charged into the reactor and carbon oxide and hydrogen as a mixed gas at a predetermined ratio is introduced into the reactor under reduced pressure or pressured condition of about 1 to 150 atms. The mixed gas is contacted with the catalyst at a space velocity of about $10^2$ to $10^5$ hr$^{-1}$. The reaction proceeds at a temperature of about 50° to about 350° C., but at a temperature below about 50° C. the catalytic activity is low and at a temperature higher than about 350° C., the catalyst may be deteriorated or the methanol produced may be decomposed. For such reason, the reaction temperature is preferably in the range of from 150° C. to 350° C. in the atmospheric and lower pressured CO—H$_2$ reactions.

The molar ratio of carbon oxide and hydrogen in reaction gas can vary widely but is generally in the range of 20:1 to 1:20. When the molar preparation of carbon oxide is higher than the above range, the conversion ratio tends to decrease whereby the process becomes economically disadvantageous. On the other hand, when the molar proportion of hydrogen is higher than the above range, the selectivity to methanol tends to decrease because of the increase in methane formation. A preferred range of the carbon oxide hydrogen molar ratio is in the range of about 5:1 to about 1:5.

The carbon oxide used in the present invention can be CO, CO$_2$ or a mixture thereof at any proportion. For example, a commercially available synthetic gas generally comprises about 85% CO and about 15% CO$_2$.

The present invention is further illustrated in more detail by the following Examples. Unless otherwise indicated, all parts, percents, ratios and the like are by weight.

EXAMPLE 1

0.90 g of palladium chloride was dissolved with stirring in a dilute aqueous hydrochloric acid (prepared from 4 ml of concentrated hydrochloric acid and 45 ml of distilled water) and 20 g of lanthanum oxide (99.9% purity, available from Nakarai Chemicals Ltd.) was added to the solution whereby the palladium salt was substantially completely supported by adsorption. Water was removed by decantation and the residue was air-dried by evaporation at 110° C. to obtain a supported powder. The resulting powder was then charged into a glass reactor, connecting with the closed recirculating system having a 420 ml content and the reactor was evacuated under reduced pressure at about 200° C. for 5 hours. Thereafter, the temperature was gradually allowed to cool to room temperature and a hydrogen gas was introduced into the reactor while gradually elevating the temperature whereby the hydrogen gas was vigorously consumed from about 50° C. and a large amount of water and hydrogen chloride was produced. The reduction with hydrogen was continued at 200° C. and was completed when the consumption of hydrogen ceased. Then, CO was introduced at 200° C. under a pressure of 20 cmHg whereby 30 ml (stp) of CO was adsorbed under substantially normal conditions. Thereafter, a mixed gas of CO (20 cmHg) and H$_2$ (45 cmHg) was introduced whereby methanol was produced at 150° to 190° C. The circulating rate of the mixed gas was 80–100 ml/minute. The results obtained on the stationary activity and the selectivity of methanol production are shown in Table 1 below. The quantitative determinations of products were conducted by gas chromatographic analysis using a column of Porapak Q 4 m (200° C.) for products in the liquid phase and by gas chromatographic analysis using a column of activated carbon 2 m (at room temperature) and a column of Al$_2$O$_3$-DMF 4 m (at room temperature) for products in the gaseous phase. In the liquid phase, methanol as well as a very small amount of HCOOCH$_3$ and ethanol were determined and, in the gaseous phase, a small amount of methane was determined.

REFERENCE EXAMPLE

The reaction between CO and H$_2$ was conducted in the same manner as described in Example 1 but using 20 g of each of zinc oxide (a reagent of Kishida Chemical Co., Ltd.) and a zinc oxide-chromium oxide catalyst (a reagent of Hashaw Chemical Company for methanol production) which had been fully reduced with hydrogen. The results obtained are also shown in Table 1 for comparative purpose.

The reaction was also conducted under the same conditions as described in Example 1 on lanthanum oxide alone used as a support but the reaction did not proceed and no product was obtained.

TABLE I

| Catalyst | Reaction Temperature (°C.) | Reaction Time (hour) | CO Conversion Ratio (mol %) | Amount of Methanol Produced (mmol) | Selectivity to Methanol (%) |
|---|---|---|---|---|---|
| PdCl$_2$-La$_2$O$_3$ | 150 | 10 | 28.2 | 1.3 | 99 |
|  | 175 | 5 | 37.2 | 1.7 | 98 |
|  | 190 | 5 | 38.0 | 1.8 | 97 |

TABLE I-continued

| Catalyst | Reaction Temperature (°C.) | Reaction Time (hour) | CO Conversion Ratio (mol %) | Amount of Methanol Produced (mmol) | Selectivity to Methanol (%) |
|---|---|---|---|---|---|
| Comparative Runs | | | | | |
| $Cr_2O_3$—ZnO (20 g) (a reagent of Hashaw Chemical Co. for methanol production) | 200 | 150 | 1.0 | 0.04 | 80 |
| ZnO (20 g) (a reagent of Kishida Chemical Co., Ltd.; 99.9% purity) | 260 | 120 | 2.1 | 0.08 | 80 |

EXAMPLE 2

In the same manner as described in Example 1, a mixed gas comprising CO (20 cmHg) and $H_2$ (40 cmHg); $CO_2$ (20 cmHg) and $H_2$ (40 cmHg); or CO (20 cmHg), $CO_2$ (10 cmHg) and $H_2$ (45 cmHg) is reacted at 200° C. on the same catalyst as used in Example 1 ($PdCl_2$-$La_2O_3$). The results on methanol production are shown in Table 2 below.

TABLE 2

| Catalyst | Composition of Reaction Gas (cmHg) | | | Reaction Time (hour) | Amount of Methanol Produced (mmol) | Selectivity to Methanol (based on consumed carbon oxide mol %) |
|---|---|---|---|---|---|---|
| | CO | $CO_2$ | $H_2$ | | | |
| $PdCl_2$—$La_2O_3$ | 20 | 0 | 40 | 5 | 1.56 | 98 |
| | 0 | 20 | 40* | 5 | 0.34 | 71 |
| | 20 | 10 | 45 | 5 | 1.79 | 95 |

*A substantial amount of CO was produced as the reaction proceeds.

EXAMPLE 3

1.0 g of palladium chloride was dissolved with stirring in a dilute aqueous hydrochloric acid and any excess of hydrochloric acid was neutralized with aqueous ammonia. To the solution were then added 20 g of each of magnesium oxide (a reagent of Nakarai Chemicals Ltd.; 99.9% purity), cerium oxide ($CeO_2$, a reagent of Iwai Chemicals, Ltd.; 99.9% purity), calcium oxide (CaO, a reagent of Merck & Co., Inc.), beryllium oxide (BeO, a reagent of Mitsuwa Chemical Co., Ltd.; 99.99% purity), neodymium oxide ($Nd_2O_3$, a reagent of Wako Pure Chemical Industries, Ltd.; 99.9% purity) and yttrium oxide ($Y_2O_3$, a reagent of Wako Pure Chemical Industries, Ltd.; 99.9% purity), and the mixture was evaporated to dryness while thoroughly stirring to obtain a supported powder. The resulting powder was reduced with hydrogen using the procedure as described in Example 1 and thereafter the reaction was conducted by introducing a mixed gas of CO and $H_2$ in the same manner as described in Example 1 to obtain methanol. The results obtained by determination of the conversion ratio of CO and the selectivity for methanol are shown in Table 3 below.

Gas chromatographic analysis of the product according to the procedure as described in Example 1 showed that the liquid phase product contained methanol as well as a very small amount of $HCOOCH_3$ and ethanol and that the gaseous phase contained a small amount of methane.

A comparative run was conducted in the same manner as described in Example 3, but using a catalyst of palladium supported on silica gel and a mixed gas of CO and $H_2$. The results obtained are also shown in Table 3 below.

TABLE 3

| Catalyst | Reaction Gas (cmHg) | | Reaction Temperature (°C.) | Reaction Time (hour) | CO Conversion Ratio (mol %) | Amount of Methanol Produced (mmol) | Selectivity to Methanol (%) |
|---|---|---|---|---|---|---|---|
| | CO | $H_2$ | | | | | |
| $PdCl_2$—MgO | 20 | 45 | 220 | 23.5 | 36 | 1.6 | 94 |
| $PdCl_2$—CaO | 20 | 45 | 200 | 23.5 | 12 | 0.56 | 89 |
| $PdCl_2$—BeO | 20 | 45 | 220 | 23.5 | 7 | 0.33 | 76 |
| $PdCl_2$—$CeO_2$ | 20 | 45 | 220 | 24 | 8.3 | 0.29 | 74 |
| $PdCl_2$—$Nd_2O_3$ | 20 | 45 | 200 | 5 | 18 | 0.85 | 95 |
| $PdCl_2$—$Y_2O_3$ | 20 | 45 | 200 | 5 | 17 | 0.84 | 96 |
| $PdCl_2$—$SiO_2$GEL* | 20 | 45 | 200 | 20 | 1.1 | 0.06 | 30 |

*WAKO C-200, a reagent of Wako Pure Chemical Industries, Ltd. which had been reduced at 300° C. for 48 hours.

EXAMPLE 4

3.0 g of palladium chloride was supported by immersion on 20 g of lanthanum oxide from a dilute hydrochloric acid and dried by evaporation at a temperature of 110° C. The resulting yellow powder was pressed by a tabletting machine to produce pellets which were then mechanically crushed to regulate a particle size of about 10 to 20 mesh (Tyler standard) and charged into a high pressure reactor made of SUS 3200 stainless steel tube having a diameter of 40 mm and a height of 500 mm, lined with a Hastelloy-C alloy plate. The apparent volume of the charged catalyst was about 10 ml and the upper and lower portions of the catalyst layer were packed with glass beads having a diameter of 2 mm. The catalyst was then reduced in a hydrogen stream at 1 atm. and at 320° C. for 5 hours. A mixed high pressure gas comprising carbon monoxide gas and hydrogen gas of research grade was reacted while passing through the catalyst layer and the results obtained are shown in Table 4 below. In these experiments, no changes have been observed in the catalytic activity and selectivity after the continuous run for about 100 hours.

reactor and reduced in a hydrogen stream at 1 atm. at 320° C. for 5 hours. A pressured mixed gas of CO and $H_2$ was then reacted while passing through the catalyst layer. The products were determined by bubbling a discharging gas in 2 absorbing towers each containing 200 ml of pure water and quantitatively analyzing the products dissolved therein by an FID gas chromatogra-

TABLE 4

| Run No. | Catalyst | Reaction Conditions | | | | Products (mmols)/Hour | | | | | | Single Stream Conversion (mol %) | Selectivity to Methanol |
|---|---|---|---|---|---|---|---|---|---|---|---|---|---|
| | | Pressure (kg/cm$^2$) | CO/H$_2$ Molar Ratio | Velocity (ml/min) | Temperature (°C.) | CH$_3$OH | C$_2$H$_5$OH | Other O-Containing Compounds | CH$_4$ | C$_2$H$_4$ C$_2$H$_6$ | Other Hydrocarbons | | |
| 1 | PdCl$_2$—La$_2$O$_3$ | 20 | 0.5 | 800 | 250 | 20.3 | 0.048 | + | 0.74 | 0.02 | — | 3.0 | 97 |
| 2 | " | 40 | 0.5 | 1,600 | 272 | 60 | 0.16 | + | 2.42 | 0.04 | — | 4.4 | 96 |
| 3 | " | 40 | 0.5 | 1,600 | 292 | 133 | 0.52 | + | 5.72 | 0.07 | — | 9.8 | 96 |
| 4 | " | 40 | 0.5 | 2,400 | 292 | 168 | 0.65 | + | 6.37 | 0.11 | — | 5.5 | 97 |
| 5 | " | 60 | 0.5 | 1,600 | 302 | 163 | 0.97 | + | 12.0 | 0.18 | — | 12.3 | 93 |
| 6 | " | 60 | 0.5 | 2,400 | 310 | 165 | 1.0 | + | 14.7 | 0.27 | — | 8.4 | 92 |

(1) The oxygen-containing products other than methanol and ethanol were small amounts of diethyl ether, propyl alcohol, methyl acetate, ethyl acetate, butyl alcohol, etc.
(2) The amount of $CO_2$ as by-product is about 0.2 to 1.2% based on the amount of CO at outlet but is not indicated in Table 4.

EXAMPLE 5

2.6 g of palladium chloride ammonium salt (NH$_4$)$_2$PdCl$_4$ (available from Kojima Chemical Co., Ltd., Japan) was supported on 16.5 g of neodymium oxide (Nd$_2$O$_3$, 99.9%; available from Wako Pure Chemical Industries, Ltd.) by immersion in an aqueous solution of palladium chloride ammonium salt and, after drying, pellets having a grain size of 4 to 8 mesh (Tyler standard) were prepared, 18 g of the pellets (an apparent volume of 15 ml) was charged into a high pressure phy analyzer (Porapak Q, 4 m, at 200° C.) and a steam gas chromatography analyzer (at 170° C., 2 m) for oxygen-containing compounds including methanol. Also, the analysis for the produced hydrocarbons, i.e., methane and ethane, $CO_2$ and unreacted CO and $H_2$ was conducted by gas chromatography using an activated carbon column (1 m, at room temperature), Al$_2$O$_3$-DMF (38% support, 4 m, at room temperature) and Porapak Q (1 m, 70° C.). The results obtained are shown in Table 5 below.

TABLE 5

| Run No. | Catalyst | Reaction Conditions | | | | Products (mmols)/Hour | | | | | | Single Stream Conversion (mol %) | Selectivity to Methanol |
|---|---|---|---|---|---|---|---|---|---|---|---|---|---|
| | | Pressure (kg/cm$^2$) | CO/H$_2$ Molar Ratio | Velocity (ml/min) | Temperature (°C.) | CH$_3$OH | C$_2$H$_5$OH | Other O-Containing Compounds | CH$_4$ | CH$_4$ C$_2$H$_6$ | Other Hydrocarbons | | |
| 1 | (NH$_4$)$_2$PdCl$_4$—Nd$_2$O$_3$ Amount of Pd supported: 55% by weight | 5 | 0.5 | 800 | 220 | 2.1 | + | — | 0.07 | 0.02 | — | 0.31 | 95 |
| 2 | (NH$_4$)$_2$PdCl$_4$—Nd$_2$O$_3$ Amount of Pd supported: 55% by weight | 10 | 0.5 | 800 | 250 | 4.2 | 0.02 | — | 0.35 | 0.02 | — | 0.65 | 93 |
| 3 | (NH$_4$)$_2$PdCl$_4$—Nd$_2$O$_3$ Amount of Pd supported: 55% by weight | 20 | 0.5 | 800 | 272 | 12.1 | 0.07 | — | 1.56 | 0.04 | — | 1.9 | 89 |
| 4 | (NH$_4$)$_2$PdCl$_4$—Nd$_2$O$_3$ Amount of Pd supported: 55% by weight | 40 | 0.5 | 800 | 292 | 50.6 | 0.38 | — | 6.7 | 0.20 | + | 8.0 | 89 |
| 5 | (NH$_4$)$_2$PdCl$_4$—Nd$_2$O$_3$ Amount of Pd supported: 55% by weight | 40 | 0.5 | 1,600 | 292 | 67.5 | 0.65 | + | 4.3 | 0.17 | + | 5.0 | 94 |
| 6 | (NH$_4$)$_2$PdCl$_4$—Nd$_2$O$_3$ Amount of Pd supported: 55% by weight | 40 | 0.5 | 1,600 | 310 | 75 | 1.08 | + | 14.0 | 0.38 | + | 6.3 | 84 |
| 7 | (NH$_4$)$_2$PdCl$_4$—Nd$_2$O$_3$ Amount of Pd supported: 55% by weight | 60 | 0.5 | 1,600 | 290 | 95 | 0.80 | + | 1.78 | 0.10 | + | 6.8 | 98 |

TABLE 5-continued

| Run No. | Catalyst | Reaction Conditions ||||  Products (mmols)/Hour |||||| Single Stream Conversion (mol %) | Selectivity to Methanol |
| | | Pressure (kg/cm$^2$) | CO/H$_2$ Molar Ratio | Velocity (ml/min) | Temperature (°C.) | CH$_3$OH | C$_2$H$_5$OH | Other O-Containing Compounds | CH$_4$ | CH$_4$ C$_2$H$_6$ | Other Hydrocarbons | | |
| --- | --- | --- | --- | --- | --- | --- | --- | --- | --- | --- | --- | --- | --- |
| 8 | (NH$_4$)$_2$PdCl$_4$—Nd$_2$O$_3$ Amount of Pd supported: 55% by weight | 40 | 0.5 | 2,400 | 312 | 88 | 1.17 | + | 8.4 | 0.23 | + | 4.6 | 91 |

(1) The oxygen-containing products other than methanol and ethanol were small amounts of diethyl ether, propyl alcohol, methyl acetate, ethyl acetate, butyl alcohol, etc.
(2) The amount of CO$_2$ as by-product is about 0.2% based on the amount of CO at outlet, but is not indicated in Table 5.

What is claimed is:

1. A method for producing methanol which comprises reacting a gas containing a carbon oxide and hydrogen in the presence of a catalyst consisting essentially of palladium supported on at least one oxide of metal selected from the group consisting of yttrium oxide, lanthanum oxide and neodymium oxide.

2. The method according to claim 1, wherein said reaction is conducted at a temperature of about 50° to about 350° C. at a space velocity of about 10$^2$ to about 10$^5$ hr$^{-1}$ using a gas having a carbon oxide:hydrogen molar ratio of about 20:1 to about 1:20.

3. The method according to claim 1, wherein said reaction is conducted at a temperature of 150° to 250° C. using a gas having a carbon oxide:hydrogen molar ratio of 5:1 to 1:5.

* * * * *